United States Patent
Qu et al.

(10) Patent No.: US 10,683,265 B1
(45) Date of Patent: Jun. 16, 2020

(54) CANNABIDIOL-3-SULFONIC ACID, PREPARATION METHOD AND APPLICATION THEREOF, AND CANNABIDIOL DERIVATIVE

(71) Applicant: Yantai Hemp Biotechnology Co., Ltd., Yantai, Shandong (CN)

(72) Inventors: Guiwu Qu, Qingdao (CN); Ming Cui, Qingdao (CN)

(73) Assignee: YANTAI HEMP BIOTECHNOLOGY CO., LTD., Yantai, Shandong (CN)

( * ) Notice: Subject to any disclaimer, the term of this patent is extended or adjusted under 35 U.S.C. 154(b) by 0 days.

(21) Appl. No.: 16/594,661

(22) Filed: Oct. 7, 2019

(30) Foreign Application Priority Data

Aug. 28, 2019 (CN) .......................... 2019 1 0800720

(51) Int. Cl.
*C07C 303/06* (2006.01)
*C07C 303/44* (2006.01)
*C07C 309/42* (2006.01)
*B01D 15/08* (2006.01)

(52) U.S. Cl.
CPC .......... *C07C 303/06* (2013.01); *C07C 303/44* (2013.01); *C07C 309/42* (2013.01); *B01D 15/08* (2013.01)

(58) Field of Classification Search
CPC ... C07C 303/06; C07C 303/44; C07C 309/42; B01D 15/08
See application file for complete search history.

(56) References Cited

U.S. PATENT DOCUMENTS 9,950,976 B1 * 4/2018 Keller .................. C07C 37/004

* cited by examiner

*Primary Examiner* — Paul A Zucker
(74) *Attorney, Agent, or Firm* — Arent Fox LLP; Michael Fainberg

(57) ABSTRACT

The present invention relates to a cannabidiol-3-sulfonic acid, a preparation method and application thereof, and a cannabidiol derivative. The present invention introduces a sulfonic acid group in a molecular structure of cannabidiol, and the sulfonic acid group as a polar group can increase the polarity of cannabidiol, thereby improving the water solubility thereof. The cannabidiol-3-sulfonic acid can be subjected to a salt forming reaction with an inorganic base or an organic base, so that the water solubility of the cannabidiol is further improved, and the druggability of a drug based on a parent nucleus and physiological activity of the CBD structure can be enhanced. The newly introduced sulfonic acid group in the cannabidiol-3-sulfonic acid provided by the present invention can be used as a new action site to react with a specific group, and the research and application range of the cannabidiol-3-sulfonic acid is further broadened.

12 Claims, 1 Drawing Sheet

CANNABIDIOL-3-SULFONIC ACID, PREPARATION METHOD AND APPLICATION THEREOF, AND CANNABIDIOL DERIVATIVE

CROSS-REFERENCE TO RELATED APPLICATIONS

This application claims priority to Chinese Patent Application No. 201910800720.9 filed on Aug. 28, 2019, the entire contents of which is hereby incorporated by reference.

TECHNICAL FIELD

The present invention relates to the technical field of medicinal chemical engineering, and in particular to a cannabidiol-3-sulfonic acid, and a preparation method and application thereof, and a cannabidiol derivative.

BACKGROUND

Cannabidiol (CBD) has the alias L-trans-cannabidiol, and has the English name (−)-cannabidiol; the English chemical name is 2-[(1R,6R)-3-methyl-6-(1-methylvinyl)-2-cyclohexen-1-yl]-5-pentyl-1,3-benzenediol; the molecular formula: $C_{21}H_{30}O_2$; molecular weight: 314.46; and CAS register number: 13956-29-1.

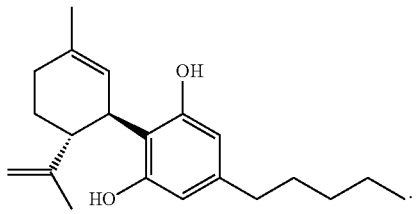 [SMILES: C=C(C)[C@@H]1CCC(C)=C[C@H]1c1c(O)cc(CCCCC)cc1O]

The cannabidiol (CBD) is one of the main phenolic chemical components in *Cannabis sativa*. It is found by in vivo experiments that the CBD not only antagonizes the mental activity caused by THC agonist cannabinoid type I receptor (CB1R), but also has anticonvulsant, sedative-hypnotic, anxiolytic, anti-psychotic, anti-inflammatory and neuroprotective effects, and is a natural active ingredient that is highly promising in the fields of pharmaceuticals and food.

In recent years, great progress has been made in the research and application development of physiological activities of the CBD. UK's GW Pharmaceuticals has developed Sative (oral mucosal spray with a THC/CBD content ratio of 1) and Epidiolex (liquid preparation for the CBD) for the treatment of tuberous sclerosis (TSC) and children epileptic seizures, respectively. AXIM® Biotech's applied research on the treatment of irritable bowel syndrome by using cannabidiol chewing gum has also entered clinical trials. In addition, great progress of the CBD has been made in the fields of food and cosmetics.

At present, the application research field of the CBD mainly focuses on drug development. A high-purity CBD is a white or light yellow crystal with a melting point of 66-67° C., almost insoluble in water or 10% sodium hydroxide solution, soluble in ethanol, methanol, ether, benzene, chloroform and petroleum ether and other organic solvents. This ester-soluble feature of the CBD makes the CBD have a major limitation in drug development.

In view of the fact that drugs with quicker absorption and higher bioavailability are required against some certain diseases clinically, improving the water solubility of the CBD has important scientific value and social value.

SUMMARY

An objective of the present invention is to provide a cannabidiol-3-sulfonic acid, a preparation method and application thereof, and a cannabidiol derivative. The cannabidiol-3-sulfonic acid has high water solubility.

In order to achieve the foregoing invention objective, the present invention provides the following technical solutions:

The present invention provides a cannabidiol-3-sulfonic acid having the structure of Formula I:

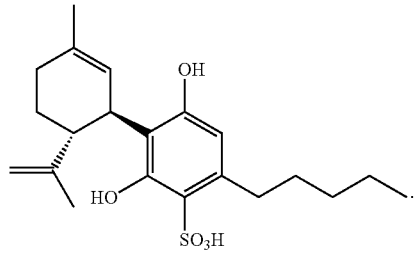

Formula I

The present invention provides a method for preparing the cannabidiol-3-sulfonic acid of the aforementioned technical solution, including the following step of:

mixing cannabidiol with concentrated sulfuric acid to carry out sulfonation reaction to obtain the cannabidiol-3-sulfonic acid.

Preferably, the molar ratio of the cannabidiol to the concentrated sulfuric acid is 1:(15-30).

Preferably, the temperature of the sulfonation reaction is 0-35° C. and the time is 2-8 h.

Preferably, after the completion of the sulfonation reaction, the method further includes: extracting the obtained reaction solution, and then purifying the extracted material.

Preferably, a method for the purification includes column chromatography and crystallization which are carried out sequentially.

Preferably, a chromatographic medium used for the column chromatography includes silica gel, gel, octadecyl bonded silica, macroporous adsorption resin or polyamide.

Preferably, a solvent used for the extraction, column chromatography and crystallization independently includes water, ethanol, methanol, ethyl acetate or petroleum ether.

The present invention provides application of the cannabidiol-3-sulfonic acid of the above technical solution in the preparation of a cannabidiol derivative, where the sulfonic acid group in the cannabidiol-3-sulfonic acid serves as a reaction site.

The present invention provides a cannabidiol derivative prepared by the application of the above technical solution, including a cannabidiol-3-sulfonate and a cannabidiol-3-sulfonamide.

The present invention provides a cannabidiol-3-sulfonic acid. The present invention introduces a sulfonic acid group in a molecular structure of cannabidiol, and the sulfonic acid group as a polar group can increase the polarity of the cannabidiol, and further improve the water solubility thereof.

The cannabidiol-3-sulfonic acid provided by the present invention can be subjected to a salt forming reaction with an inorganic base or an organic base, and the obtained cannabidiol-3-sulfonate has better water solubility, can further increase the water solubility of the cannabidiol derivative, and increase the druggability of a drug based on a parent nucleus and physiological activity of the CBD structure.

In addition, on the premise of ensuring that the parent nucleus of the basic structure of the cannabidiol is not greatly changed, the newly introduced sulfonic acid group in the cannabidiol-3-sulfonic acid provided by the present invention can be used as a new action site to react with a specific group, and the research and application range of the cannabidiol-3-sulfonic acid can be further broadened.

DETAILED DESCRIPTION

Figure 1:
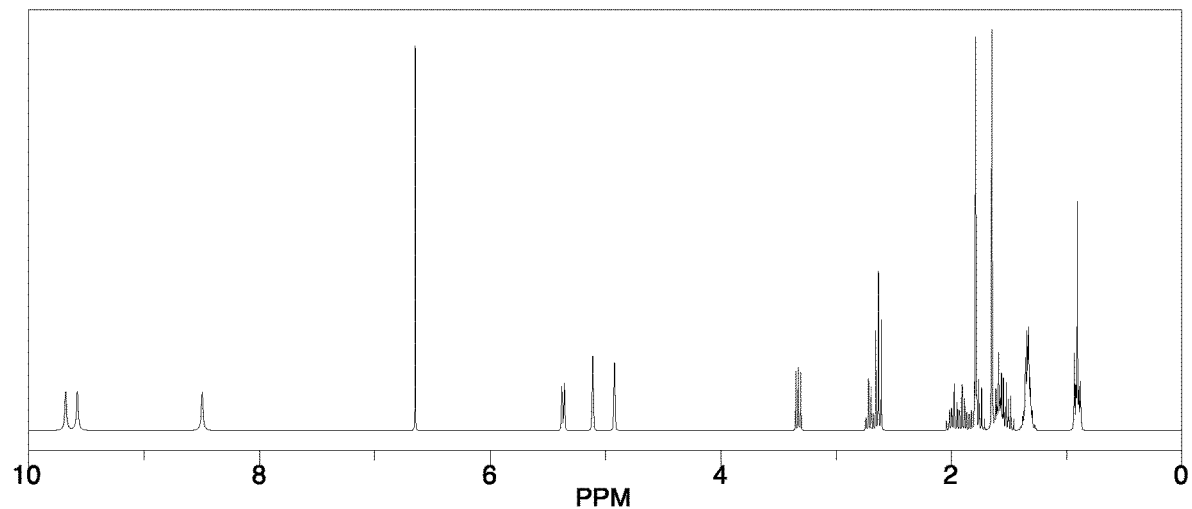
FIG. 1 is a hydrogen spectrogram of a cannabidiol-3-sulfonic acid prepared in Embodiment 1.

The present invention provides a cannabidiol-3-sulfonic acid having the structure of Formula I:

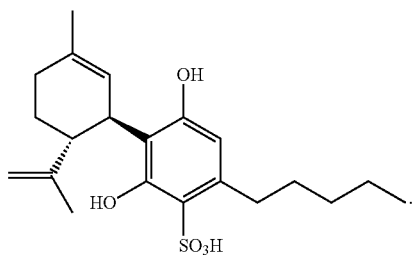

Formula I

In the present invention, the full name of the chemical name of the cannabidiol-3-sulfonic acid is: (1'R,2'R)-2,6-dihydroxy-5'-methyl-4-pentyl-2"-(propyl-1-en-2-yl)-1''',2', 3',4'-tetrahydro-[1,1'-biphenyl]-3-sulfonic acid. In the cannabidiol-3-sulfonic acid provided by the present invention, the introduction of a sulfonic acid group as a polar group into the structure of cannabidiol can enhance the polarity of the cannabidiol and therefore increase the water solubility thereof.

The present invention provides a method for preparing the cannabidiol-3-sulfonic acid according to the aforementioned technical solution, including the following step of:

mixing cannabidiol with concentrated sulfuric acid to carry out sulfonation reaction to obtain the cannabidiol-3-sulfonic acid.

In the present invention, the required preparation raw materials are all commercially available products well known to those skilled in the art unless otherwise specified.

The present invention mixes cannabidiol with concentrated sulfuric acid to carry out sulfonation reaction to obtain the cannabidiol-3-sulfonic acid. In the present invention, the concentrated sulfuric acid is preferably commercially available concentrated sulfuric acid, namely a concentrated sulfuric acid having a mass fraction of 98%.

In the present invention, the molar ratio of the cannabidiol to the concentrated sulfuric acid is preferably 1:(15-30), more preferably 1:(20-25). In the present invention, the mixing process preferably includes: first adding concentrated sulfuric acid into a flask with three necks, cooling the concentrated sulfuric acid to 0° C. by an ice-water bath, adding cannabidiol, controlling the temperature to be lower than 15-25° C., so that the feeding is completed, and the mixing is completed.

In the present invention, the temperature of the sulfonation reaction is preferably 0-35° C., more preferably 10-30° C., most preferably 15-25° C., and the time is preferably 2-8 h, more preferably 3-6 h, most preferably 4-5 h. In the sulfonation reaction process, a sulfonic acid group on the concentrated sulfuric acid is introduced into the structure of the cannabidiol to obtain a cannabidiol-3-sulfonic acid having the sulfonic acid group.

In the present invention, after the completion of the sulfonation reaction, preferably the method further includes: extracting the obtained reaction solution, and then purifying the extracted material. In the present invention, the extraction is preferably carried out in an ice-water bath. After the extraction is completed, the organic phase extracted is purified; and a method for the purification preferably includes column chromatography and crystallization which are carried out sequentially.

In the present invention, a chromatographic medium used for the column chromatography preferably includes silica gel, gel, octadecyl bonded silica, macroporous adsorption resin or polyamide; and a solvent used for the extraction, column chromatography and crystallization preferably independently includes water, ethanol, methanol, ethyl acetate or petroleum ether. The present invention does not specifically limit the specific process of the column chromatography, and a process well known to those skilled in the art may be selected.

In the embodiment of the present invention, when column chromatography is performed using silica gel, specifically, the organic phase extracted is concentrated under reduced pressure at 50° C., and then subjected to a 200-300 mesh silica gel column; the organic phase is eluted with 2-3 column volumes of eluent 1 (the ratio of petroleum ether to ethyl acetate to methanol is 8:1:1) and then is eluted with 2-3 column volumes of eluent 2 (the ratio of the petroleum ether to the ethyl acetate to the methanol is 4:1:2); the part eluted by the eluent 2 is collected; after drying under reduced pressure, an appropriate amount of methanol is added at room temperature until the solid is all dissolved; the solution stands at room temperature and naturally volatilizes until a crystal appears, and then the crystal is transferred to an environment at 5-10° C. and stands for 2-5 h to obtain a cannabidiol-3-sulfonic acid.

In the embodiment of the present invention, when the macroporous adsorption resin is used for column chromatography, specifically, the organic phase extracted is dried under reduced pressure at 50° C. and then dissolved in a 10% ethanol solution; the sample is loaded to an AB-8 type macroporous adsorption resin column; the sample is first washed with 3-5 column volumes of 10% ethanol and then washed with 2-3 column volumes of 50% ethanol, and finally the column is washed with 2-3 column volumes of 95% ethanol; the part eluted by the 50% ethanol is collected; after drying under reduced pressure, an appropriate amount of absolute ethanol is added until the solid matter is completely dissolved, the solution stands at room temperature and naturally evaporates until a crystal appears, and then the crystal is transferred to an environment at 5-10° C. and stands for 2-5 h to obtain a cannabidiol-3-sulfonic acid.

The present invention provides application of the cannabidiol-3-sulfonic acid of the above technical solution in the preparation of a cannabidiol derivative, where the sulfonic acid group in the cannabidiol-3-sulfonic acid serves as a reaction site. In the present invention, the sulfonic acid group introduced in the cannabidiol-3-sulfonic acid can be used as a new chemical action site, and can be used for the preparation of a cannabidiol derivative without major changes in the molecular structure of cannabidiol.

In the embodiment of the present invention, the cannabidiol-3-sulfonic acid can be used for the preparation of a cannabidiol-3-sulfonate (taking a sodium cannabidiol-3-sulfonate as an example), and the preparation method preferably includes the following steps of:

pouring the reaction solution obtained by the sulfonation reaction described in the above technical solution into a saturated NaCl solution (20-time volumes) to carry out salting out, and subjecting the obtained precipitate to suction filtration, and washing the precipitate with a saturated NaCl solution until the precipitate is near-neutral, dissolving the obtained filter cake in hot water, adjusting the pH to neutral, filtering the filter cake while the filter cake is hot, and refrigerating at 5-10° C. to obtain the sodium cannabidiol-3-sulfonate (colorless crystal). In the present invention, the ratio of the mass of the hot water to the mass of the filter cake is preferably 5:1, and the temperature of the hot water is preferably 70-90° C. In the present invention, a base used for adjusting the pH preferably includes an inorganic base or an organic base, more preferably includes NaOH, Ca(OH)$_2$, Mg(OH)$_2$, ethanolamine or pyridine; and the base is preferably used in the form of a solution. The mass fraction of the alkali solution is not particularly limited, and those skilled in the art can adjust the mass fraction according to actual needs; and in the embodiment of the present invention, the mass fraction of the NaOH solution used is preferably 10%.

In the present invention, the sodium cannabidiol-3-sulfonate can be acidified by equimolar hydrochloric acid and extracted with ethyl acetate to obtain the cannabidiol-3-sulfonic acid, that is, the cannabidiol-3-sulfonic acid and the cannabidiol-3-sulfonate can be converted to each other. The present invention does not particularly limit the process of acidification by the hydrochloric acid and extraction by the ethyl acetate, and a method well known to those skilled in the art may be selected.

In the present invention, the cannabidiol-3-sulfonate can further increase the water solubility of the cannabidiol-3-sulfonic acid.

In the present invention, the cannabidiol-3-sulfonic acid can be used for preparing cannabidiol-3-sulfonamide. The present invention does not particularly limits a method for preparing the cannabidiol-3-sulfonamide by using the cannabidiol-3-sulfonic acid, and a method well known to those skilled in the art may be selected.

The present invention provides a cannabidiol derivative prepared by the application of the above technical solution, including a cannabidiol-3-sulfonate and a cannabidiol-3-sulfonamide.

In the present invention, the cannabidiol-3-sulfonate is preferably sodium cannabidiol-3-sulfonate, and the structural formula is:

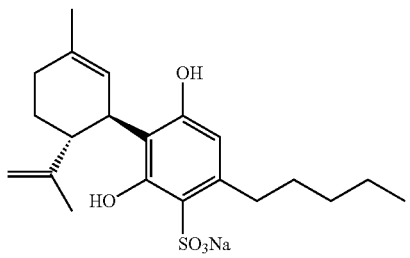

In the present invention, the structural formula of the cannabidiol-3-sulfonamide is:

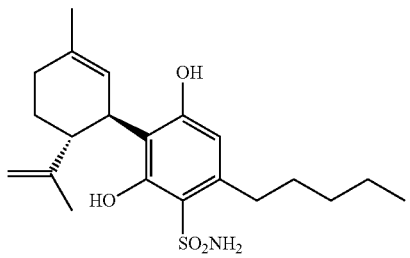

The technical solutions in the present invention will be clearly and completely described below in conjunction with the embodiments of the present invention. Apparently, the described embodiments are merely some embodiments rather than all of the embodiments of the present invention. All other embodiments obtained by a person of ordinary skill in the art based on the embodiments of the present invention without creative efforts shall fall within the protection scope of the present invention.

Embodiment 1

Cannabidiol and the concentrated sulfuric acid reacted according to a molar ratio of 1:15.

50 g of concentrated sulfuric acid was weighed and added into a flask with three necks and naturally cooled to 0° C. by an ice-water bath, 10.68 g of cannabidiol was added, and the temperature was controlled to be below 20° C.; after the feeding, the temperature was controlled at 20° C., and sulfonation reaction was performed for 4 h; the reaction was stopped, and the obtained reaction solution was poured into the ice-water bath for extraction by ethyl acetate; the extracted organic phase was concentrated under reduced pressure at 50° C. and then subjected to a 200-300 mesh silica gel column, and the organic phase was eluted with 2 column volumes of eluent 1 (the ratio of petroleum ether to ethyl acetate to methanol was 8:1:1) and then was eluted with 3 column volumes of eluent 2 (the ratio of the petroleum ether to the ethyl acetate to the methanol was 4:1:2); the part eluted by the eluent 2 was collected; after drying under reduced pressure, an appropriate amount of methanol was added at room temperature until the solid was all dissolved; the solution stood at room temperature and naturally volatilized until a crystal appeared, and then the crystal was transferred to an environment at 5-10° C. and stood for 2-5 h to obtain a colorless needle-shaped crystal compound (9.46 g).

High-resolution mass spectrometry analysis showed that the molecular weight of the compound was 394.53, and by hydrogen spectrum (see FIG. 1) analysis, it was confirmed that the structure of the compound was cannabidiol-3-sulfonic acid. The structural formula is as follows:

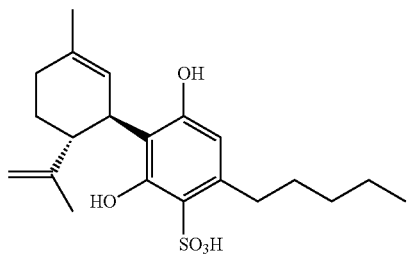

Embodiment 2

Cannabidiol and the concentrated sulfuric acid reacted according to a molar ratio of 1:30.

50 g of concentrated sulfuric acid was weighed and added into a flask with three necks and naturally cooled to 0° C. by an ice-water bath, 5.34 g of cannabidiol was added, and the temperature was controlled to be below 15° C.; after the feeding, the temperature was controlled at 25° C., and sulfonation reaction was performed for 2 h; the reaction was stopped, and the obtained reaction solution was poured into the ice-water bath for extraction by ethyl acetate; the organic phase extracted was dried under reduced pressure at 50° C. and then dissolved in a 10% ethanol solution; the sample was loaded to an AB-8 type macroporous adsorption resin column; the sample was first washed with 5 column volumes of 10% ethanol and then washed with 3 column volumes of 50% ethanol, and finally the column was washed with 3 column volumes of 95% ethanol; the part eluted by the 50% ethanol was collected; after drying under reduced pressure, an appropriate amount of absolute ethanol was added until the solid matter was completely dissolved, the solution stood at room temperature and naturally evaporated until a crystal appeared, and then the crystal was transferred to an environment at 5-10° C. and stood for 2-5 h to obtain a colorless needle-shaped crystal, namely a cannabidiol-3-sulfonic acid (4.37 g).

Embodiment 3

Cannabidiol and concentrated sulfuric acid reacted according to a molar ratio of 1:20.

50 g of concentrated sulfuric acid was weighed and added into a flask with three necks and naturally cooled to 0° C. by ice-water bath, 8 g of cannabidiol was added, and the temperature was controlled to be below 25° C.; after the feeding, the temperature was controlled at 35° C., and sulfonation reaction was performed for 2 h; the reaction was stopped, and an obtained reaction solution was poured into a saturated NaCl solution which was 20 times the volume of the reaction solution, and solution stood; after the precipitation was complete, the precipitate was subjected to suction filtration and washed with a saturated NaCl solution until the precipitate was near-neutral, the obtained filter cake was dissolved at 80° C. in hot water which was 5 times the weight of the filter cake, the pH was adjusted to near-neutral with 10% NaOH solution, the solution was filtered while hot and refrigerated at 5-10° C. to obtain a colorless crystal, namely sodium cannabidiol-3-sulfonate (5.87 g).

By high-resolution mass spectrometry analysis, the results indicated that the molecular weight of the product was 416.51. By preparation process analysis, it can be learned that the sample prepared was sodium cannabidiol-3-sulfonate. The structural formula is as follows:

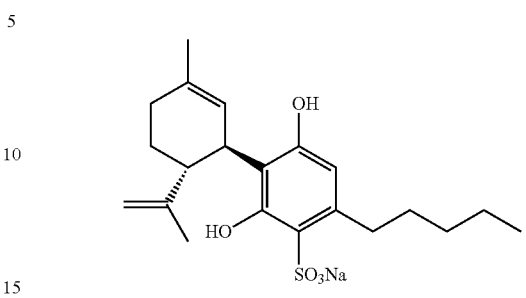

1 g of the aforementioned sodium cannabidiol-3-sulfonate was taken and dissolved in 10 mL of 0.25 mol·L$^{-1}$ hydrochloric acid solution and extracted with an equal volume of ethyl acetate, and after the obtained organic phase was naturally volatilized to dry the solvent, it was showed by high-resolution mass spectrometry analysis that the molecular weight of the compound was 394.18. It can be learned according to the preparation process that the sample prepared is cannabidiol-3-sulfonic acid, that is, the sodium cannabidiol-3-sulfonate can be converted into the cannabidiol-3-sulfonic acid.

Embodiment 4

The addition of the sulfonic acid group has added a new action site for cannabidiol, making it possible to carry out structural modification of cannabidiol without major changes in the parent nucleus of the basic structure. This embodiment describes this using the cannabidiol-3-sulfonamide as an example.

The synthetic route of the cannabidiol-3-sulfonamide is:

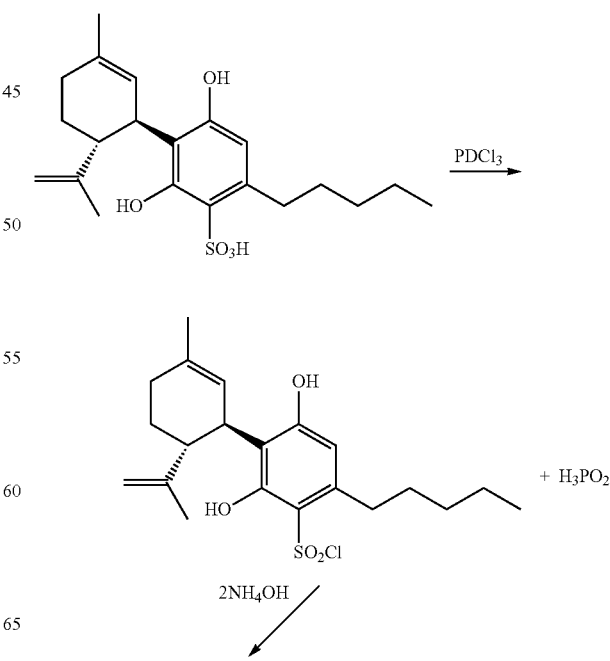

-continued

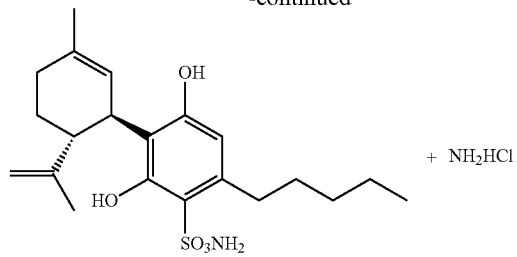

+ NH₂HCl

The specific synthesis process is as follows:

Step 1) of Preparation of cannabidiol-3-sulfonyl chloride 5 g of cannabidiol-3-sulfonic acid (prepared in Embodiment 1) was weighed and added to 50 g of phosphorus oxychloride, and reflux reaction was performed for 15 h; after the reaction was completed, the obtained reaction solution was poured into 1 L of ice/water mixture, extraction was performed three times with dichloromethane, and the amount of the dichloromethane used was 500 mL every time; the organic extracts were combined and washed with saline water and then an appropriate amount of magnesium sulfate was added for drying, filtration was performed, the solution was concentrated under reduced pressure to 50 ml, equivoluminal n-hexane was added into the solution, the solution was stirred for 30 min and filtered, and the obtained filter cake was washed with 100 mL of dichloromethane/n-hexane (1:1, v/v) to obtain cannabidiol-3-sulfonyl chloride (3.9 g).

Step 2) of Preparation of cannabidiol-3-sulfonamide

Under ice bath conditions, the abovementioned 3.9 g of cannabidiol-3-sulfonyl chloride was slowly added to 20 mL of concentrated ammonia water (adding with stirring), the ice bath was stopped, and the solution continued to be stirred and reacted for 10 min; 15 ml of water was added, and the solution was slowly heated to 30° C.; the solution was stirred for 30 min to remove excess ammonia, and at this time, the reaction mixture was a gray paste; the mixture was cooled in an ice bath and subjected to suction filtration and washed with a small amount of ice water, dried, dissolved in methanol and crystallized to obtain a target product (2.7 g).

Figure 2:
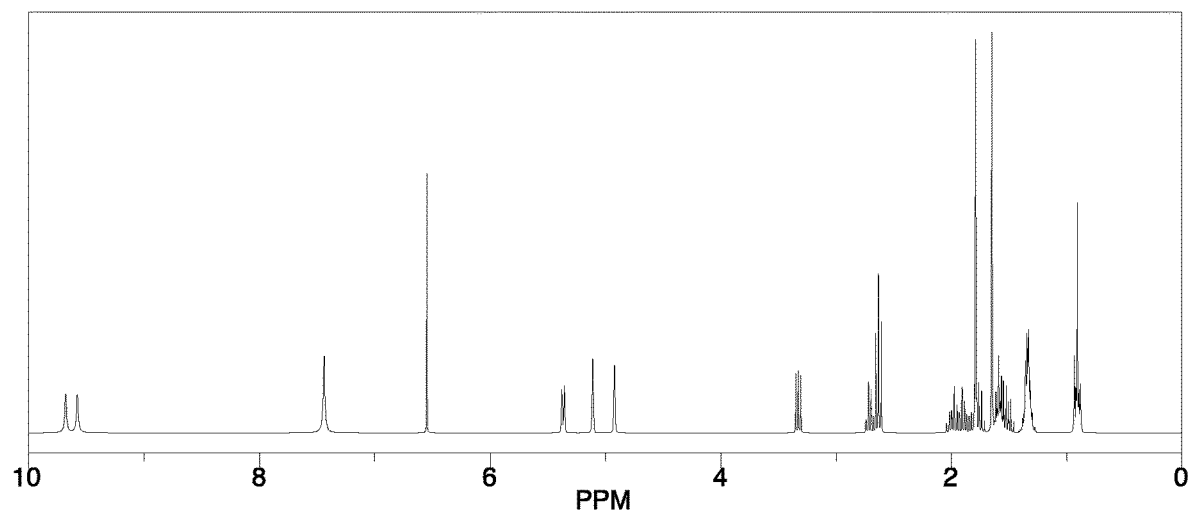
FIG. 2 is a hydrogen spectrogram of a cannabidiol-3-sulfonamide prepared in Embodiment 4.

By high-resolution mass spectrometry analysis, the mass spectrometry analysis results of the obtained target product showed that the molecular weight was 393.54, and it was analyzed with reference to the hydrogen spectrogram (see FIG. 2) that the structure of the target product was cannabidiol-3-sulfonamide, and the structural formula is as follows:

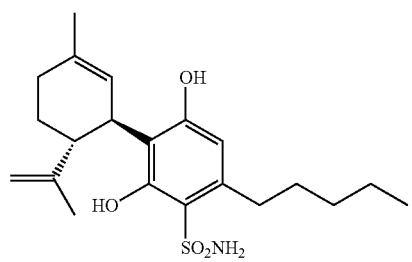

It can be seen from Embodiment 4 that the sulfonic acid group in the cannabidiol-3-sulfonic acid provided by the present invention can also be combined as a new action site with a specific group, making it possible to perform structural modification of cannabidiol under the conditions that the parent nucleus of the basic structure is not subjected to major changes.

Test Example

1. Solubility Determining:

1) Instruments and reagents: Thermo Fisher UltiMate 3000 high performance liquid chromatography (Thermo, USA); chromatographic column (Phenomenex Gemini C18, 5μ, 250×4.6 mm); electronic balance (METTLER TOLEDO instruments (Shanghai) Co., Ltd.); cannabidiol (commercially available), cannabidiol-3-sulfonic acid (prepared in Embodiment 1) and sodium cannabidiol-3-sulfonate (prepared in Embodiment 3). chromatography acetonitrile (Merck, Germany); water was Milli-Q ultrapure water, the remaining reagents were analytically pure.

2) Solution Preparation

Three clean 10 mL penicillin bottles were taken, 6 mL of ultrapure water was added accurately in each of the penicillin bottles, and the weight was weighed accurately. Cannabidiol, cannabidiol-3-sulfonic acid and sodium cannabidiol-3-sulfonate were separately added at room temperature until ultrasonic treatment was performed for 10 min and the samples still could not be completely dissolved, to obtain saturated solutions of three compounds respectively; the solutions stood overnight at room temperature, and supernatants were taken as solutions of samples for test (supernatants of the cannabidiol-3-sulfonic acid and the sodium cannabidiol-3-sulfonate were diluted by appropriate times depending on the detection situation).

An appropriate amount of cannabidiol, cannabidiol-3-sulfonic acid and sodium cannabidiol-3-sulfonate were taken and were prepared into solutions with a concentration of 0.2 mg·mL$^{-1}$ as reference substance solutions by using 10% acetonitrile-0.5% acetic acid solution.

2) Sample Detection

The samples were determined by high performance liquid chromatography (Appendix V D of Part II of Chinese Pharmacopoeia).

Chromatographic conditions and system suitability Octadecylsilane bonded silica was used as a filler; 10% acetonitrile—0.5% acetic acid→75% acetonitrile—0.5% acetic acid were used as mobile phases; the wavelength was detected to be 225 nm; and the theoretical plate numbers were not less than 4,000 on a basis of cannabidiol, cannabidiol-3-sulfonic acid and sodium cannabidiol-3-sulfonate.

A measurement method includes: precisely measuring and injecting 20 μL of solution of sample for test into a liquid chromatograph, and recording a chromatogram; and taking a reference substance solution and measuring the reference substance solution according to the same method. The concentrations of the three compounds in the solution of sample for test were calculated by an external standard method according to a peak area. The specific results are shown in Table 1.

TABLE 1

| | | Cannabidiol-3-sulfonic acid | Sodium cannabidiol-3-sulfonate |
|---|---|---|---|
| Compound | Cannabidiol | | |
| Solubility (mg · mL$^{-1}$) | 0.41 | 56.21 | 485.77 |

It can be seen from Table 1 that the cannabidiol was slightly soluble in water at room temperature, but after the introduction of the sulfonic acid group, the solubility was increased to 56.21 mg·mL$^{-1}$; and after the salt formation, the solubility was as high as 485.77 mg·mL$^{-1}$, which can satisfy requirements for solubility of general injection medicines.

It can be seen from the above embodiment that the present invention provides a cannabidiol-3-sulfonic acid, a preparation method and application thereof, and a cannabidiol derivative. Relative to cannabidiol, the cannabidiol-3-sulfonic acid provided by the present invention is obviously improved in water solubility, the cannabidiol-3-sulfonic acid can further be subjected to a salt forming reaction with an inorganic base or an organic base, so that the water solubility of the cannabidiol compound is further improved, and the druggability of a drug based on a parent nucleus and physiological activity of the CBD structure is enhanced. In addition, on the premise of ensuring that the parent nucleus of the basic structure of the cannabidiol is not greatly changed, the newly introduced sulfonic acid group in the cannabidiol-3-sulfonic acid provided by the present invention can be used as a new action site to react with a specific group, and the research and application range of the cannabidiol-3-sulfonic acid can be further broadened.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A cannabidiol-3-sulfonic acid, wherein the cannabidiol-3-sulfonic acid has the structure of Formula I:

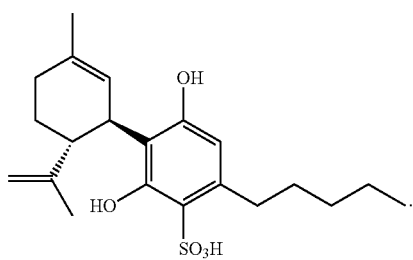

Formula I

2. A method for preparing a cannabidiol-3-sulfonic acid having the structure of Formula I:

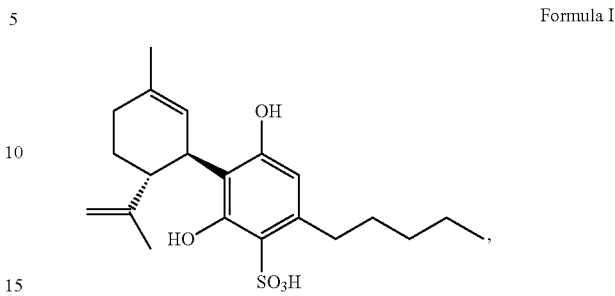

Formula I, wherein the method comprises:
mixing cannabidiol with concentrated sulfuric acid to carry out a sulfonation reaction to obtain the cannabidiol-3-sulfonic acid.

3. The preparation method according to claim 2, wherein the molar ratio of the cannabidiol to the concentrated sulfuric acid is 1:15.

4. The preparation method according to claim 2, wherein the sulfonation reaction is performed at a temperature of 0-35° C. and a time of 2-8 h.

5. The preparation method according to claim 2, wherein after completion of the sulfonation reaction, the method further comprises:
extracting the obtained reaction solution to obtain an extracted material, and
purifying the extracted material.

6. The preparation method according to claim 5, wherein purifying the extracted material comprises column chromatography and crystallization which are carried out sequentially.

7. The preparation method according to claim 6, wherein the chromatographic medium used for the column chromatography comprises silica gel, gel, octadecyl bonded silica, macroporous adsorption resin or polyamide.

8. The preparation method according to claim 5, wherein the solvent used for the extraction, column chromatography and crystallization independently comprises water, ethanol, methanol, ethyl acetate or petroleum ether.

9. The preparation method according to claim 6, wherein the solvent used for the extraction, column chromatography and crystallization independently comprises water, ethanol, methanol, ethyl acetate or petroleum ether.

10. The preparation method according to claim 7, wherein the solvent used for the extraction, column chromatography and crystallization independently comprises water, ethanol, methanol, ethyl acetate or petroleum ether.

11. The preparation method according to claim 2, wherein the molar ratio of the cannabidiol to the concentrated sulfuric acid is 1:20.

12. The preparation method according to claim 2, wherein the molar ratio of the cannabidiol to the concentrated sulfuric acid is 1:30.

* * * * *